(12) United States Patent
Wadhwa et al.

(10) Patent No.: US 8,338,374 B2
(45) Date of Patent: Dec. 25, 2012

(54) STABLE GROWTH HORMONE LIQUID FORMULATION

(75) Inventors: Manpreet S Wadhwa, Thousand Oaks, CA (US); Sandeep Nema, St. Louis, MO (US); Advait Badkar, Wildwood, MO (US)

(73) Assignee: Pharmacia Corporation, St. Louis, MO (US)

( * ) Notice: Subject to any disclaimer, the term of this patent is extended or adjusted under 35 U.S.C. 154(b) by 215 days.

(21) Appl. No.: 10/583,923

(22) PCT Filed: Dec. 13, 2004
(Under 37 CFR 1.47)

(86) PCT No.: PCT/IB2004/004159
§ 371 (c)(1),
(2), (4) Date: May 14, 2007

(87) PCT Pub. No.: WO2005/063298
PCT Pub. Date: Jul. 14, 2005

(65) Prior Publication Data
US 2008/0125356 A1 May 29, 2008

Related U.S. Application Data

(60) Provisional application No. 60/531,843, filed on Dec. 23, 2003.

(51) Int. Cl.
*A61K 38/27* (2006.01)
*A61K 38/17* (2006.01)
*A61K 38/18* (2006.01)
*A61K 47/42* (2006.01)

(52) U.S. Cl. .............. 514/11.4; 424/198.1; 424/497; 530/351

(58) Field of Classification Search .............. None
See application file for complete search history.

(56) References Cited

U.S. PATENT DOCUMENTS

| | | | | |
|---|---|---|---|---|
| 5,206,219 | A | | 4/1993 | Desai .............. 514/3 |
| 5,272,135 | A | | 12/1993 | Takruri .............. 514/12 |
| 5,358,708 | A | * | 10/1994 | Patel .............. 424/85.1 |
| 6,448,225 | B2 | * | 9/2002 | O'Connor et al. .............. 514/12 |
| 6,525,102 | B1 | * | 2/2003 | Chen et al. .............. 424/85.2 |
| 6,593,296 | B1 | | 7/2003 | McNamara et al. .............. 514/12 |
| 2002/0077461 | A1 | * | 6/2002 | Bjorn et al. .............. 530/399 |
| 2003/0082234 | A1 | | 5/2003 | Seo et al. .............. 424/486 |
| 2003/0162711 | A1 | | 8/2003 | Bjorn et al. .............. 514/12 |

FOREIGN PATENT DOCUMENTS

| | | | |
|---|---|---|---|
| WO | WO9403198 | | 2/1994 |
| WO | WO9714430 | | 4/1997 |
| WO | WO 97/29767 | * | 8/1997 |
| WO | WO9729767 | | 8/1997 |
| WO | WO9739768 | | 10/1997 |
| WO | WO9915193 | | 4/1999 |
| WO | WO 0103741 | | 1/2001 |
| WO | WO0217957 | | 3/2002 |

OTHER PUBLICATIONS

Feng et al, Biotechnology Techniques, Apr. 1998, vol. 12, No. 4, pp. 289-293.*
Bio-Rad laboratories, product sheet, 2000, pp. 1-4.*
Cleland et al, Pharmaceutical research, 1996, vol. 13, No. 10, pp. 1464-1475.*
Serajuddin et al, Journal of Pharmaceutical Sciences, 1990, vol. 79, No. 5, pp. 463-464.*
Jin Yin et al., Pharmaceutical Research, vol. 21, No. 12., Dec. 2004, pp. 2377-2383.
Kozlov et al., Macromolecules, vol. 33, pp. 3305-3313, 2000.
Bam et al., Journal of Pharmaceutical Sciences, 1991, vol. 87, No. 12, p. 1554-1559.

* cited by examiner

*Primary Examiner* — Bridget E Bunner
*Assistant Examiner* — Fozia Hamud
(74) *Attorney, Agent, or Firm* — John A. Wichtowski (57) ABSTRACT

The present invention is directed to stable liquid growth hormone formulations that remain stable after physical agitation, and after exposure to one or more freeze-thaw events. Formulations of the present invention can be stored long term at a variety of temperatures, even frozen. In the present invention, a combination of buffer and stabilizing agents, including a non-ionic surfactant (e.g., polysorbate 20), a polymer stabilizer (e.g., polyethylene glycol), and other optional stabilizers combine to provide unexpected stability to aqueous formulations of a growth hormone (e.g., human growth hormone).

14 Claims, 7 Drawing Sheets

STABLE GROWTH HORMONE LIQUID FORMULATION

The present application claims priority under Title 35, United States Code, §119 to U.S. Provisional application Ser. No. 60/531,843 filed Dec. 23, 2003, which is incorporated by reference in its entirety as if written herein.

FIELD OF THE INVENTION

The present invention relates to stable liquid formulations of growth hormones, such as human growth hormone, particularly, to such formulations that remain stable after long term storage, and also remain stable after being subjected to physical stress such as agitation, freezing, and thawing.

BACKGROUND OF THE INVENTION

Native human growth hormone is a single polypeptide chain protein consisting of 191 amino acids, internally cross-linked by two disulphide bridges. The growth hormones of other animal species are closely homologous to native human growth hormone, and have similar biological activity in terms of being effective in the treatment of diseases related to growth hormone deficiencies in humans, such as hypopituitary dwarfism and osteoporosis. Recombinant forms of human growth hormone have also been produced with the same or substantially similar amino acid sequence as native human growth hormone and identical biological activity to the native hormone. Except as otherwise noted below, all native and recombinant forms of human growth hormone are collectively referred to as "hGH." Because of the structural similarities between hGH and the growth hormones of other species, one would expect formulations that are effective in stabilizing hGH to also be effective in stabilizing the growth hormones of other species.

hGH is primarily sold in lyophilized form today. See, for example, GENOTROPIN® Lyophilized Powder (Pharmacia & Upjohn Company, now owned by Pfizer Inc.), HUMATROPE® (Eli Lilly), NORDITROPIN® for Injection (Novo Nordisk), SAIZEN® for Injection (Serono), and NUTROPIN® (Genentech). Lyophilized formulations have the advantage of providing protein stability for long periods of time. However, a lyophilized formulation must be used shortly after reconstitution, as aggregation and deamidation tend to begin shortly after reconstitution with an aqueous diluent. This generally means that it is left up to the consumer of a lyophilized formulation to reconstitute the product shortly before use. If reconstitution is not done properly, or if the reconstituted formulation is stored for too long before use, the consumer may get an improper dosage of the growth hormone or a dosage containing unsuitable levels of hGH degradation products. In addition, manufacture of lyophilized formulations involves substantially greater cost and time relative to manufacture of liquid formulations.

Due to the above disadvantages with lyophilized hGH formulations, various liquid formulations of hGH have been developed over the years, each with varying degrees of stability under various storage and handling conditions. Two commercial liquid formulations of hGH are sold under the brand names NUTROPIN AQ® (Genentech, Inc.) and NORDITROPIN® (Novo Nordisk). The composition of these and other hGH liquid formulations have been disclosed in issued patents and published patent applications, summarized below. Each of the following references states that the liquid formulations of hGH formulations described therein are stable at refrigeration temperatures, at about 2° C. to about 8° C., except where noted otherwise below. However, none claim to disclose formulations that can withstand exposure to freezing and thawing, conditions to which products can be exposed in transit. Furthermore, the hGH in some of the previously disclosed formulations degrades or undergoes aggregation when subjected to physical agitation, for example, during shipment. These types of instabilities not only cause wastage of expensive product, but can also cause safety issues if the degraded product is inadvertently administered to a patient.

U.S. Pat. No. 5,567,677 (invented by Castensson et al.; assigned to PHARMACIA AB) discloses an aqueous formulation consisting of growth hormone and citrate buffer in an amount of 2-50 mM at a pH of about 5.0 to 7.0. The '677 patent also teaches that mannitol and glycine can be suitably included in the formulation disclosed therein.

U.S. Pat. Nos. 5,763,394 and 5,981,485 (invented by O'Connor et al.; assigned to GENENTECH, INC.) disclose an aqueous human growth hormone formulation containing hGH, a buffer providing pH 5.5 to pH 7 (e.g., sodium citrate), 0.1% to 1% w/v non-ionic surfactant (e.g., polysorbate 20) and, 50 to 200 mM of a neutral salt (e.g. sodium chloride), and a preservative (e.g. phenol), wherein said formulation is free of glycine and mannitol.

U.S. Pat. No. 6,022,858 (invented by Sorensen et al., assigned to NOVO NORDISK A/S), discloses a buffered aqueous solution containing a human growth hormone pretreated with zinc salt, and optionally containing lysine or calcium ion.

U.S. Pat. No. 5,849,704 (invented by Sorensen et al., assigned to NOVO NORDISK A/S), discloses a buffered aqueous solution containing a growth hormone buffered with histidine or histidine derivative.

U.S. Pat. No. 5,977,069, U.S. Pat. No. 5,631,225, and U.S. Pat. No. 5,547,696 (invented by Sorensen et al., assigned to NOVO NORDISK A/S), disclose buffered aqueous solutions containing a human growth hormone with stabilizing amounts of the amino acids asparagine, isoleucine, or valine, respectively.

U.S. Pat. No. 5,705,482 and U.S. Pat. No. 5,552,385 (invented by Christensen et al., assigned to NOVO NORDISK A/S), disclose buffered aqueous solutions containing a human growth hormone with stabilizing amounts of the peptides Leu-His-Leu and Lys-Gly-Asp-Ser respectively.

WO 01/03741 A1 (for an invention by Siebold et al.; assigned to GRANDIS BIOTECH GMBH) discloses a "storage stable liquid growth hormone formulation consisting essentially of growth hormone in isotonic phosphate buffered solution" and also claims formulations with phosphate buffer and a non-ionic surfactant present at a concentration of 0.2% or less. In the Examples section of the publication, the only non-ionic surfactant used is Pluronic F-68 at a concentration of 0.2% (w/v) in each of the formulations where it was included.

WO 02/067989 A1 (for an invention by Seibold et al.; assigned to GRANDIS BIOTECH GMBH) is directed to "an aqueous growth hormone formulation comprising growth hormone and (a) citrate buffer of about pH 5.6 or more, or (b) a buffer other than citrate of about pH 6.0 or more, and substantially free of crystallization on storage." The only suitable temperatures for storage of the disclosed formulations are refrigeration temperature (4° C. to 8° C.) and above, or in a temperature range of 8° to 25° C.

U.S. Application Publication No. 2002/0077461 (for an invention by Bjorn et al.; assigned to NOVO NORDISK OF NORTH AMERICA INC.) discloses pharmaceutical formulations comprising growth hormone (e.g., hGH), an amino acid selected from the group consisting of asparagine, isoleucine, valine, leucine, histidine, a derivative of histidine, or a peptide comprising at least one basic amino acid residue and at least one acidic amino acid residue, and a non-ionic detergent (e.g., a polysorbate or a polyaxamer). The application also discloses such formulations with a buffer, (e.g. histidine, citrate, tartrate, or phosphate) for pH 6 to pH 8, a tonicity agent (e.g., mannitol). The only stability studies disclosed in this application were carried out at refrigerated temperatures or above.

WO 01/24814 A1 (for an invention by Chen et al.; assigned to CHIRON CORPORATION) discloses the use of an amino acid base sufficient to decrease aggregate formation during storage to stabilize aqueous polypeptide formulations, where the amino acid base comprises at least one amino acid selected from the group consisting of arginine, lysine, aspartic acid, and glutamic acid. This published application also discloses the inclusion of additional stabilizers in such formulations, including antioxidants, such as methionine, and non-ionic surfactants. Interleukin-2 is the only polypeptide whose stabilization using such a formulation is illustrated therein.

The commercial formulations of liquid hGH presently available on the market include phenol as a preservative. See, for example, NUTROPIN AQ® (a liquid formulation of recombinant hGH sold by Genentech Inc.), and NORDITROPIN® (a liquid formulation of recombinant hGH sold by Novo Nordisk). However, phenol is known to promote the aggregation of hGH, especially upon freezing and thawing (see Maa, Yuh-Fun, et al., *Internat J Pharm* 140: 155-168 (1996)).

Even with all the advancements that have been made to date in the development of formulations that stabilize growth hormones in particular and polypeptides in general, the stability of hGH in liquid formulations remains a problem. Stability is particularly problematic in liquid hGH formulations exposed to freezing and subsequent thawing, especially when a phenolic excipient (e.g. phenol preservative) is present. Even a single freeze-thaw can render known liquid hGH formulations, such as the commercial formulations cited above, unsuitable for human use, due to protein aggregation and precipitate formation.

There is a need for a liquid hGH formulation that remains stable under freeze-thaw conditions, as well as under other conditions of physical stress, such as physical agitation, provided the formulation also remains stable after long term storage, under suitable storage conditions. Such a formulation could be stored not only in a refrigerator, as are the current commercial hGH formulations, it could also be stored in a freezer.

BRIEF SUMMARY OF THE INVENTION

The present invention relates to a stable liquid formulation comprising a therapeutic amount of growth hormone in an aqueous solution, a buffer, a non-ionic surfactant, and a polymer stabilizer, wherein the formulation remain stable after exposure to at least one freeze-thaw event. The liquid growth hormone formulation of the present invention can be frozen and thawed at least once without visible precipitates being formed in the formulation, and without significant loss of growth hormone from solution.

One embodiment of the invention is directed to a formulation comprising a therapeutically effective amount of growth hormone in an aqueous solution, a buffer that maintains the pH of the formulation at a pH of about 5 to about 7, a non-ionic surfactant, and a polymer stabilizer, wherein the formulation remains stable after at least one time freezing and subsequent thawing.

Another embodiment is directed to a formulation comprising, about 0.1 mg/ml to about 20 mg/ml of a recombinant form of human growth hormone in an aqueous solution, a citrate or edetate buffer that maintains the formulation at a pH of about 5 to about 7, about 0.04% to about 5% (w/w) of a polysorbate surfactant, and about 0.001% to about 20% (w/v) of polyethylene glycol, wherein the formulation remains stable after at least one freeze thaw event. In a specific embodiment the formulation remains stable after at least three freeze thaw events. In a specific embodiment the formulation remains stable after at least six freeze thaw events.

The liquid formulations of the present invention are stable in the presence or absence of phenolic preservatives, such as phenol, even after exposure to multiple freeze-thaw events. This result is surprising, in view of what is presently known regarding the effect of phenolic compounds on the aggregation of growth hormone. (See, e.g., Maa, Yuh-Fun, et al., supra).

The formulations of the present invention are also surprisingly stable under conditions of physical handling and agitation, such as the agitation that formulations are exposed to in the process of being shipped from one part of a country to another, or from one part of the World to another.

The formulations of the present invention are, furthermore, surprisingly resistant to degradation during recommended conditions of long term storage, such as storage under refrigeration from 2 to 8° C. In a specific embodiment the formulation remains stable for at least 52 weeks of storage at 2 to 8° C. The present formulations are even resistant to degradation after storage at temperatures at or below freezing.

As used herein, the terms "human growth hormone" and "hGH" refer to human growth hormone produced by methods including extraction and purification from natural human tissue sources, and from recombinant culture systems transformed with deoxyribonucleic acid encoding for human growth hormone. The sequence and characteristics of hGH are set forth, for example, in Hormone Drugs, Gueriguian et al., U.S.P. Convention, Rockville Md. (1982). The same terms, as used herein, also refer to agonist analogues of hGH, which contain substitution, deletion, and/or insertion of amino acids. The same terms, as used herein, also refer to agonist analogues of hGH having at least 40%, 50%, 60%, 70%, 80%, 90%, 95%, 96%, 97%, 98% or 99% identity to native 191 amino acid form of hGH. Two species of hGH of particular note include the 191 amino acid native species (somatotropin) and the 192 amino acid N-terminal methionine (met) species (somatrem) commonly obtained through recombinant means.

As used herein, the term "therapeutically effective amount" of hGH refers to that amount that provides a therapeutic effect in an administration regimen.

As used herein, the term "freeze-thaw event" refers to exposure of a liquid solution or other formulation to a temperature less than its freezing point, typically in a freezer at minus 20° C. or minus 70° C. until the solution is frozen, followed by thawing at a temperature greater than its freezing point, typically at 2 to 8° C. in a refrigerator, or at ambient room temperature. Samples frozen and thawed two or more times according to this procedure are said to have undergone multiple freeze-thaw events.

DETAILED DESCRIPTION OF THE INVENTION

The therapeutically effective amount of hGH in any given embodiment of the formulation of the present invention will depend upon the volume of the formulation to be delivered to any given subject, as well as the age and weight of the subject, and the nature of the illness or disorder being treated. When the formulation is to be delivered to a human subject, the formulation contains at least about 0.1 mg/ml to about 20 mg/ml hGH, about 0.5 mg/ml to about 15 mg/ml hGH, or about 1 mg/ml to about 10 mg/ml hGH.

The buffer included in the formulation of the present invention maintains the pH of the formulation at about pH 5 to about pH 7. In another embodiment, the buffer maintains the pH of the formulation at about pH 5.7 to about pH 6.5. In yet another embodiment, the buffer maintains the pH of the formulation at about pH 6. Any buffer that is capable of maintaining the pH of the formulation within any pH range given above is suitable for use in the formulations of the present invention, provided that it does not react with other components of the formulation to cause visible precipitates to form after one or more freeze-thaws or after shipment agitation, or otherwise cause the growth hormone to be chemically destabilized. The buffer used in the present formulation comprise a component selected from the group consisting of citrate, succinate, malate, edetate, histidine, acetate, adipate, aconitate, ascorbate, benzoate, carbonate, bicarbonate, maleate, glutamate, phosphate, and tartarate. Particular buffers include either edetate or citrate as components. Examples of suitable buffers for use in the formulations of the present invention include, but are not limited to, sodium citrate, sodium edetate, sodium succinate, and histidine hydrochloride. Specific embodiments are sodium edetate and sodium citrate buffers.

The buffer is present in a concentration sufficient to maintain the pH of the formulation within the pH range described above. The concentration of buffer in the formulation is about 1 mM to about 100 mM, alternatively about 2 mM to about 50 mM, or alternatively about 4 mM to about 20 mM.

The non-ionic surfactant and polymer stabilizer used in the formulation of the present invention are selected for their capacity to stabilize hGH without causing hGH or other components of the formulation to precipitate out of solution after undergoing at least one freeze-thaw event or after undergoing handling and physical agitation. The non-ionic surfactant may be a polysorbate, a poloxamer or pluronic, or another ethylene/polypropylene block polymer. In one particular embodiment the non-ionic surfactant is a polysorbate, which may be polysorbate 20 and polysorbate 80.

The polymer stabilizer included in the liquid formulation of the present invention is selected from the group consisting of polyethylene glycol and polyethylene glycol derivatives. In an a exemplary embodiment, the polymer stabilizer is polyethylene glycol of any molecular weight, within an average molecular weight range of about 400 to about 100,000 kDa, and specifically a molecular weight range of about 3000 to about 20,000 kDa. Many commercial forms of poly(ethylene) glycol (also known as "PEG") are available in these molecular weight ranges, including PEG 400, PEG 3350, PEG 8000, and PEG 20,000. In the formulations of the present invention, the addition of poly(ethylene) glycols of various molecular weights has been found to improve the stability of hGH towards physical agitation as well as freeze-thaws.

The non-ionic surfactant and polymer stabilizer are each present in a sufficient amount that the surfactant and stabilizer together stabilize the hGH formulation to physical agitation as well as freeze-thaws. In another embodiment the amount of surfactant present in the formulation is an amount that would stabilize the hGH formulation to physical agitation, even in the absence of the polymer stabilizer.

The use of non-ionic surfactants such as Polysorbates and Poloxamers at a concentration of 0.1% or greater to stabilize hGH liquid formulations has been previously disclosed (U.S. Pat. Nos. 5,763,394 and 5,981,485 (O'Connor et al.; GENENTECH); EP 0955062 A1 (O'Connor et al.; GENENTECH). The only two types of commercially available hGH liquid formulations utilize Polysorbate 20 at 0.2% (NUTROPIN AQ®), and Poloxamer 188 at 0.3% (NORDITROPIN®). Unexpectedly, it has been discovered that the liquid formulations of the present invention provide excellent hGH physical stability, even with non-ionic surfactant concentrations well below 0.1%.

The non-ionic surfactant in the stable liquid hGH formulation of the present invention is present at a concentration of at least about 0.02% (w/w) to about 10% (w/w), alternatively at a concentration of about 0.04% (w/w) to about 5% (w/w), or alternatively at a concentration of about 0.05% (w/w) to about 1% (w/w).

The polymer stabilizer is present at a concentration of at least about 0.001%, and is suitably present at a concentration of up to 70%. In formulations where it is desired that the viscosity is kept to a minimum, for example, to facilitate delivery of the formulation by injection, a relatively low concentration of polymer stabilizer is used. Under such conditions, the polymer stabilizer is present at a concentration of about 0.001% to about 20%, alternatively about 0.01% to about 10%, or alternatively about 0.05% to about 5%.

In another embodiment, the formulation of the present invention further comprises a tonicity agent. The tonicity agent may also acts as a further stabilizing agent in the hGH liquid formulation of the present invention. Suitable tonicity agents include neutral salts and carbohydrates, such as sugar alcohols, monosaccharides, and disaccharides. Suitable carbohydrate tonicity agents include non-reducing mono-, di-, or polysaccharides, or polyols, or neutral salts, including mannitol, sorbitol, lactitol, xylitol, sucrose trehalose, sodium chloride and potassium chloride. The carbohydrate tonicity agent may be mannitol, sorbitol, sucrose or trehalose, or sorbitol. Formulations of the present invention prepared with each of the last four tonicity agents have been found to be stable after exposure to freeze-thaw events, physical agitation and long term storage. However, sorbitol was found to have a stabilizing effect on the hGH against physical agitation in the absence of other stabilizers. This is surprising, since for a previously disclosed liquid hGH formulation, the use of mannitol as a tonicity agent and stabilizer has been demonstrated (e.g., U.S. Pat. No. 5,567,677), and in yet another case, the use of sodium chloride as a tonicity agent and stabilizer has been demonstrated (see, for example, U.S. Pat. No. 5,763,394).

When a tonicity agent is present, it may be present in an amount sufficient to make the formulation isotonic, and suitable for parenteral injection into a mammal, such as a human subject, into dermal, subcutaneous, or intramuscular tissues. Depending upon the concentrations of the other components in the formulation, sorbitol is present at a concentration of about 50 mM to about 500 mM, alternatively about 100 mM to about 400 mM, or alternatively about 200 mM to about 300 mM.

In yet another embodiment, the present formulation further comprises an amino acid stabilizer. Various amino acid stabilizers have been reported to stabilize proteins, including hGH in liquid formulations (See, for example use of glycine in U.S. Pat. No. 5,567,677 (Carstensson et al.; PHARMACIA) and use of histidine, valine, isoleucine, asparagine, and lysine, in various patents (Sorensen et al., NOVO NORDISK, supra). The amino acid stabilizer included in the formulation is one that adds further chemical stability to the formulation upon storage, without causing any physical instability after one or more freeze-thaw events, or after exposure to physical agitation. Cysteine was unexpectedly found to reduce the chemical stability of the hGH liquid formulations of the present invention, when present therein. Methionine, on the other hand has been found to improve the chemical stability of hGH in the present formulations.

The use of methionine as an antioxidant in protein formulations has been reported in the literature, since proteins tend to undergo spontaneous oxidation. However, methionine has not been reported to stabilize hGH in liquid formulations. In fact, it was observed that methionine did not improve the chemical stability of hGH, nor its oxidation profile to any significant extent when the polymer stabilizer component of the present formulation was absent. Unexpectedly, in the presence of a polymer stabilizer, such as polyethylene glycol, the addition of methionine was observed to have a beneficial effect on stability.

In another embodiment, the formulation further comprises a divalent cation. The formulation is not limited by the nature of the divalent cation. Exemplary divalent cations are magnesium, calcium, and zinc. The divalent cation may be a magnesium containing salt, such as magnesium chloride, magnesium sulfate, or magnesium hydroxide. The amount of magnesium containing salt in the formulation is present at a molar concentration that is less than molar concentration of the buffer, so as not to greatly reduce the buffering capacity of the buffer by complexation, but sufficiently high to improve the chemical stability of the formulation.

In another embodiment, the formulation optionally comprises a preservative, such as phenol and benzyl alcohol. The amounts of preservative in the formulation is present at a relatively low concentration that does not chemically or physically destabilize the hGH, and yet is present at a sufficient concentration that provides adequate antimicrobial activity for preservative action.

A particular embodiment of the present invention is a formulation comprising about 0.1 mg/ml to about 20 mg/ml of a recombinant form of human growth hormone in an aqueous solution, about 4 to about 20 mM of an edetate or citrate buffer that maintains the formulation at a pH of about 6, about 0.05% (w/w) to about 1% (w/w) of a polysorbate surfactant, and about 0.05% (w/w) to about 5% (w/w) of a polyethylene glycol polymer, wherein the formulation remains stable after at least one freeze thaw event. In a specific embodiment the formulation remains stable after at least three freeze thaw events. In a specific embodiment the formulation remains stable after at least six freeze thaw events. This embodiment of the present formulation optionally includes a tonicity agent, as described above. This embodiment of the formulation also optionally includes methionine, as described above. This embodiment of the formulation also optionally includes a magnesium reagent, as described above. This embodiment of the formulation further optionally includes a preservative, as described above.

Formulations of the present invention remain stable after exposure to a single, and even multiple freeze-thaw events. Formulations of the present invention also remain stable after exposure to physical agitation, such as one would expect to encounter upon shipping product from one location to another. Stability can be measured by any one of a number of different ways, including visual inspection for precipitate formation, analysis of percent protein remaining in solution after exposure to stress conditions (e.g., by size-exclusion HPLC for hGH monomer or by protein absorbance analysis for total hGH), or analysis of the formation of chemical variants of growth hormone (e.g., by anion exchange or reverse phase HPLC analysis). In one embodiment of the present invention, no precipitate visible to the naked eye is formed in the formulation after at least one freeze thaw event. In a specific embodiment the formulation remains stable after at least three freeze thaw events. In a specific embodiment the formulation remains stable after at least six freeze thaw events. In another embodiment, at least 90%, of the hGH monomer in the formulation remains in solution as measured by size exclusion HPLC assay after at least one freeze thaw event.

Formulations of the present invention also provide at least 90% of hGH monomer in solution by size exclusion HPLC assay, and further remain fully bioactive after storage for at least 4 weeks at 25° C., or after storage for at least 52 weeks at about 2 to 8° C. Due to their resistance to freeze-thaw conditions, formulations of the present invention can suitably be stored for extended periods of time at temperatures below freezing.

Formulations of the present invention also provide at least 90%, specifically at least 95%, specifically at least 99%, specifically at least 99.88%, and specifically at least 99.92% recovery of hGH in solution as measured by size exclusion HPLC.

Formulations of the present invention also provide at least 85%, specifically at least 86%, and specifically at least 88% recovery of hGH in solution as measured by reverse phase HPLC.

Formulations of the present invention also provide less than 7%, specifically less than 6% deamidation in solution as measured by anion exchange HPLC.

The complete content of all publications, patents, and patent applications cited in this disclosure are herein incorporated by reference as if each individual publication, patent, or patent application were specifically and individually indicated to be incorporated by reference.

The present invention is further illustrated by the following examples. These examples are intended to be illustrative of the invention and should not be used to limit or restrict its scope.

EXAMPLES

The following examples illustrate one or more of the embodiments of the formulations of the hGH formulation of the present invention, described above. In each of the formulations of the present invention tested below, was somatotropin, a recombinant form of hGH. The somatotropin used in the Examples below, is the same hGH protein found in commercial forms of Genotropin® (PHARMACIA & UPJOHN COMPANY). For more information about Genotropin®, see Physician's Desk Reference, 57th ed., pub. by Thompson P D R at Montvale, N.J. (2003). The examples, below, also compare the physical stability of hGH formulations of the present invention to the physical stability of known hGH liquid formulations.

Example 1

Physical Stability of Known hGH Liquid Formulations

Somatotropin was used to prepare an aqueous hGH formulation disclosed in U.S. Pat. No. 5,567,677 (Castensson et al., assigned to PHARMACIA AB). The hGH formulation had the following composition: 5 mg/ml hGH, 5 mM sodium citrate, pH 6.2, 12 mM glycine, and 250 mM mannitol. This formulation is hereinafter referred to as the "CGM" formulation.

Vials of a commercially available hGH aqueous formulation, NUTROPIN AQ® were obtained. The composition of NUTROPIN AQ®, according to the product label, was: 5 mg/ml hGH, 10 mM sodium citrate, 8.7 mg/ml sodium chloride, 2 mg/ml (0.2%) Polysorbate 20, and 2.5 mg/ml (0.25%) phenol. The composition of this formulation has also been disclosed in U.S. Pat. No. 5,763,394.

Cartridges of a commercially available hGH aqueous formulation, NORDITROPIN® were also obtained. The composition of NORDITROPIN®, according to the product label, was: 3.3 mg/ml hGH, 0.67 mg/ml histidine, 40 mg/ml mannitol, 3 mg/ml (0.3%) Poloxamer 188, and 3 mg/ml (0.3%) phenol.

The three formulations described above were tested for stability after being exposed to physical stress, including freeze-thaw events and physical agitation. Freezing was conducted in a −20° C. freezer; subsequent thawing was conducted at approx 5° C. in a refrigerator; and the process was repeated up to 6 times. The physical agitation test was conducted at approx 5° C. using a mechanical shaker platform at 250 revolutions per minute ("RPM") for about 20 hours. The physical agitation test was designed to simulate harsh agitation conditions that may sometimes occur during shipping. Stability of the formulations was evaluated by hGH monomer concentration assay using size exclusion high pressure liquid chromatography (hereinafter, "SE-HPLC") after each such test. Assay values of greater than 90% were considered acceptable.

The CGM formulation was found to be stable after exposure to multiple freeze-thaw events, and essentially 100% of the protein was recovered by hGH monomer concentration analysis. However, this formulation was found unstable upon exposure to physical agitation at 5° C. A cloudy precipitate was formed in the vials after agitation, and less than 10% of the protein was recovered in solution by SE-HPLC analysis.

In contrast, the commercially available formulations were found to be stable after physical agitation but unstable after exposure to multiple freeze-thaw events. Specifically, both commercial formulations tested remained clear, and essentially 100% protein was recovered after forced agitation at 5° C. However, both of the commercial formulations turned cloudy after only a single freeze-thaw event, and only about 30% protein was found in solution by SE-HPLC concentration analysis after exposure to six freeze-thaw events.

Figure 1:
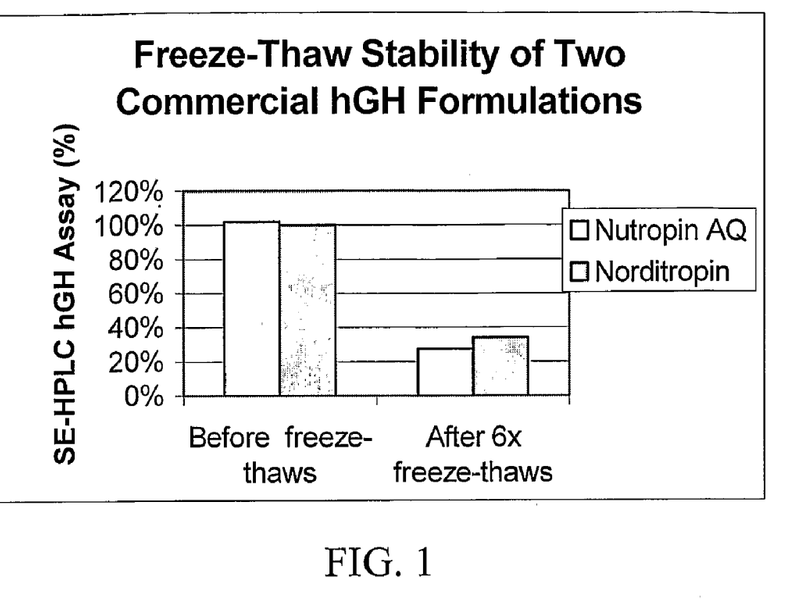
FIG. 1 is a bar graph showing the percent of hGH recovered, measured by size-exclusion HPLC analysis, from commercially available liquid hGH formulations before and after being exposed to six freeze-thaw events, as described in Example 1.

A plot of the results of SE-HPLC analysis of the three formulations after exposure to either physical agitation or six freeze-thaw events can be found in FIG. 1. These results are summarized in Table I, below. As one can see from Table I and FIG. 1, each of the known hGH liquid formulations tested in this Example is unstable under conditions of at least one form type of physical stress, whether that stress is due to physical agitation, or due to exposure to freezing and thawing.

TABLE I

| Formulation | Stability to Forced Agitation | Stability to Freeze-Thaws |
|---|---|---|
| "CGM" | No | Yes |
| NUTROPIN AQ ® | Yes | No |
| NORDITROPIN ® | Yes | No |

Example 2

Physical Stability of hGH Liquid Formulations with and without Phenol and with a Polysorbate Surfactant and Poly(ethylene)glycol ("PEG")

Four hGH liquid formulations were prepared as shown in Table II, below, with somatotropin, edetate buffer, polysorbate surfactant, PEG, and additional excipients. Three concentrations of hGH (1, 5, and 10 mg/ml) are represented within the first three formulations (Formulations 1, 2, and 3, respectively), and the fourth formulation (Formulation 4) contains 5 mg/ml of hGH and 0.3% phenol, as a preservative.

TABLE II

| | Formulation | | | |
|---|---|---|---|---|
| Composition | 1 | 2 | 3 | 4 |
| hGH Concentration | 1 mg/ml | 5 mg/ml | 10 mg/ml | 5 mg/ml |
| Buffer | 10 mM Sodium Edetate | 10 mM Sodium Edetate | 10 mM Sodium Edetate | 10 mM Sodium Edetate |
| Surfactant Stabilizer | 0.06% Polysorbate 20 | 0.06% Polysorbate 20 | 0.06% Polysorbate 20 | 0.06% Polysorbate 20 |
| Polymer Stabilizer | 1% PEG 3350 | 1% PEG 3350 | 1% PEG 3350 | 1% PEG 3350 |
| Preservative | — | — | — | 0.3% Phenol |
| Additional Excipients | 250 mM Sorbitol, 10 mM Methionine, 3 mM Magnesium Chloride | 250 mM Sorbitol, 10 mM Methionine, 3 mM Magnesium Chloride | 250 mM Sorbitol, 10 mM Methionine, 3 mM Magnesium Chloride | 250 mM Sorbitol, 10 mM Methionine, 3 mM Magnesium Chloride |

As in Example 1, the formulations prepared as described immediately above were tested for physical stability by SE-HPLC, after exposure to six freeze-thaws. The formulations were also tested for physical stability after agitation by shipping the formulations three times between two cities (Skokie, Ill. and Chesterfield, Mo.), while keeping them refrigerated at 2° C. to 8° C. using gel cold packs.

Figure 2:
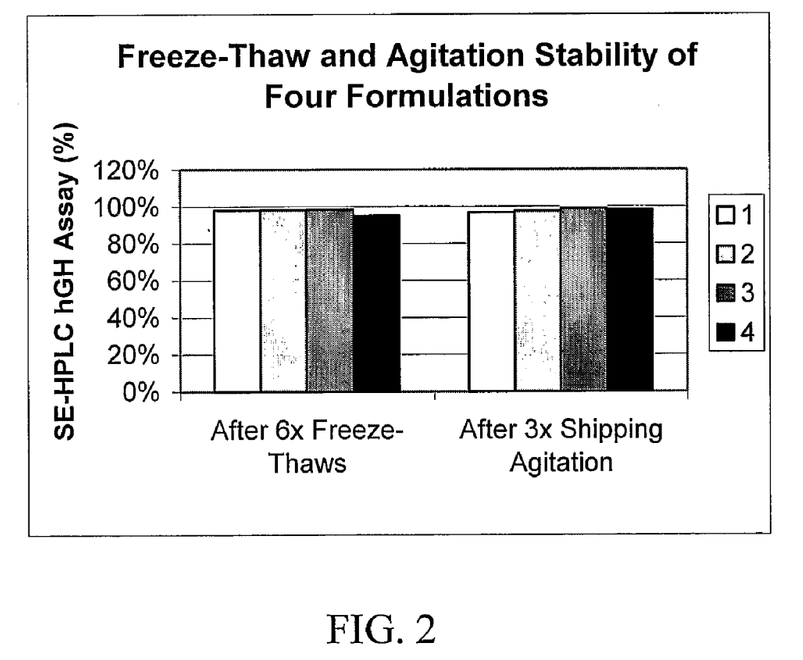
FIG. 2 is a bar graph showing the percent of hGH recovered, measured by size-exclusion HPLC analysis, from liquid hGH formulations of the present invention after exposure to freeze-thaws, and after exposure to shipment agitation, as described in Example 2.

Results of SE-HPLC analysis of each formulation after each physical stability test described above are illustrated in FIG. 2. Better than 90% hGH recovery was obtained for all four formulations tested, demonstrating very good physical stability to freeze-thaws as well as to agitation. Good stability to freeze-thaws was also obtained even when phenol was present, in contrast to the results observed with the commercial phenol-containing hGH liquid formulations tested as described in Example 1. This was surprising, considering the fact that phenol is known to promote aggregation of recombinant hGH (see Maa, Yuh-Fun, et al., supra).

Also surprisingly, good stability to agitation was obtained even when the surfactant concentration was at 0.06%. This concentration of surfactant in the hGH formulations tested in this example is much less than the 0.2 to 0.3% concentration of non-ionic surfactants in the two commercial hGH liquid formulations tested in Example 1. It is also considerably less than the concentration range of 0.1 to 1% claimed in U.S. Pat. No. 5,763,394.

Example 3

Physical and Chemical Stability of hGH Formulations Prepared with Various Polysorbate Surfactants and PEG of Differing Molecular Weights Four liquid formulations of hGH (Formulations 5 through 8) were prepared as described in Table III, below, formulations containing 5 mg/ml somatotropin, citrate buffer, a polysorbate surfactant, a PEG polymer, and additional excipients. Three different molecular weights of PEG (3350, 8000, and 20000) as well as two PEG concentrations (0.25% and 1%) were included in one of each of the formulations. A simulated version of the commercially available NUTROPIN AQ® was also prepared, according to the formula provided on the product label, as described in Example 1, above, as a comparator.

TABLE III

| | Formulation | | | |
|---|---|---|---|---|
| Composition | 5 | 6 | 7 | 8 |
| hGH concentration | 5 mg/ml | 5 mg/ml | 5 mg/ml | 5 mg/ml |
| Buffer | 5 mM Sodium Citrate | 5 mM Sodium Citrate | 5 mM Sodium Citrate | 5 mM Sodium Citrate |
| Surfactant Stabilizer | 0.06% Polysorbate 20 | 0.06% Polysorbate 20 | 0.06% Polysorbate 20 | 0.06% Polysorbate 20 |
| Polymer Stabilizer | 1% PEG 3350 | 1% PEG 8000 | 1% PEG 20000 | 0.25% PEG 20000 |
| Additional Excipients | 250 mM Sorbitol, 10 mM Methionine | 250 mM Sorbitol, 10 mM Methionine | 250 mM Sorbitol, 10 mM Methionine | 250 mM Sorbitol, 10 mM Methionine |

As in Example 1, each of the formulations prepared as described in the present Example, above, was tested for physical stability by SE-HPLC, after exposure to six freeze-thaw events and to forced agitation stress. All the Genotropin® formulations remained visually clear and better than 90% hGH recovery, as measured by SE-HPLC, was obtained for all of Formulations 5 through 8 of Table III, after being subjected to either type of physical stress. In contrast, in the simulated version of NUTROPIN AQ®, visual cloudiness was observed after freeze-thaw events; and, on average, only approximately 70% hGH monomer recovery was obtained.

Each of the formulations was also analyzed by Anion Exchange HPLC (AEX-HPLC) to evaluate the formation of hGH protein variants after 6 months refrigerated storage at 2° C. to 8° C., and after 6 weeks storage at 25° C. Although, at least some of the hGH variants detected by AEX-HPLC were known to be therapeutically active, this method provided a relative measure of hGH chemical stability. Specifically, this assay method allows one to measure the levels of hGH variants formed over time, including deamidated species.

Figure 3:
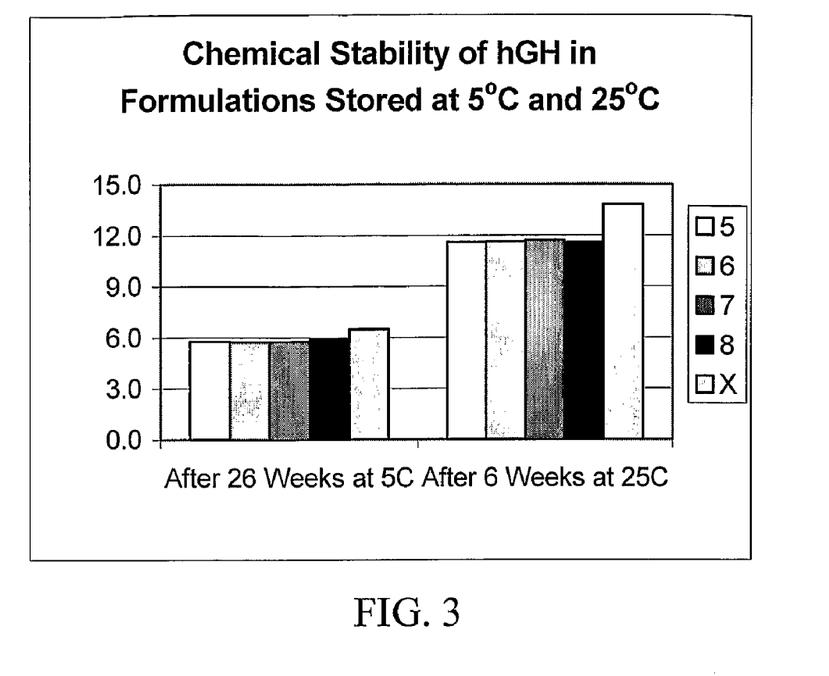
FIG. 3 is a bar graph of the total percent of hGH variants formed, measured with anion-exchange HPLC, from hGH liquid formulations of the present invention, in comparison to a previously known hGH liquid formulation, after six months storage at 5° C., and after six weeks storage at 25° C., as described in Example 3.

The results of the AEX-HPLC assay are illustrated in FIG. 3. The results depicted therein demonstrate that AEX-HPLC detected similar levels of hGH variants for all the Genotropin formulations at each temperature. The levels of variants were lower in Formulation 5 through 8, compared to those found in the simulated NUTROPIN AQ® formulation (Formulation X in FIG. 3). These results indicate excellent chemical stability relative to a known hGH liquid formulation, even apart from excellent physical stability. The data also demonstrates that different molecular weights and concentrations of PEG polymer can be used to produce hGH liquid formulations with similar chemical and physical stability.

Example 4

Physical and Chemical Stability of hGH Formulations Prepared with Polysorbate Surfactant, PEG, and Various Buffers Six hGH liquid formulations (Formulations 9 through 14), containing 5 mg/ml somatotropin, various buffers, a polysorbate surfactant, a PEG polymer, and additional excipients were prepared, as described in Table IV, below. Six different buffers at 50 mM strength (citrate, succinate, malate, edetate, bicarbonate and histidine) were used to prepare one of each of the formulations, at pH 6.

TABLE IV

| | Formulation | | | | | |
|---|---|---|---|---|---|---|
| Composition | 9 | 10 | 11 | 12 | 13 | 14 |
| hGH concentration | 5 mg/ml | 5 mg/ml | 5 mg/ml | 5 mg/ml | 5 mg/ml | 5 mg/ml |
| Buffer | 50 mM Sodium Citrate | 50 mM Sodium Succinate | 50 mM Sodium Malate | 50 mM Sodium Edetate | 50 mM Sodium Bicarbonate | 50 mM Histidine Hydrochloride |
| Surfactant Stabilizer | 0.06% Polysorbate 20 | 0.06% Polysorbate 20 | 0.06% Polysorbate 20 | 0.06% Polysorbate 20 | 0.06% Polysorbate 20 | 0.06% Polysorbate 20 |
| Polymer Stabilizer | 1% PEG 20000 | 1% PEG 20000 | 1% PEG 20000 | 1% PEG 20000 | 1% PEG 20000 | 1% PEG 20000 |
| Additional Excipients | 250 mM Sorbitol, 10 mM Methionine | 250 mM Sorbitol, 10 mM Methionine | 250 mM Sorbitol, 10 mM Methionine | 250 mM Sorbitol, 10 mM Methionine | 250 mM Sorbitol, 10 mM Methionine | 250 mM Sorbitol, 10 mM Methionine |

All six formulations tested were found have very good physical stability. Specifically, all six formulations were found to be stable after exposure to agitation and to six freeze-thaw events, as described in Example 2.

Figure 4:
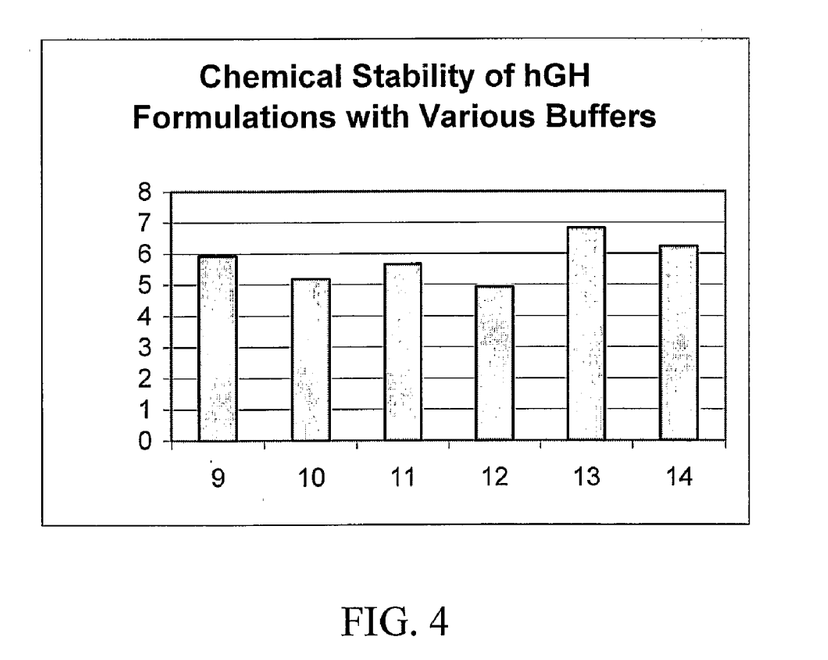
FIG. 4 is a bar graph of the total percent of hGH variants, measured with anion-exchange HPLC, from hGH liquid formulations of the present invention, prepared with various buffers, after 18 weeks storage at 5° C., as described in Example 4.

The six formulations were also tested for chemical stability using AEX-HPLC, after 18 weeks of storage at 5° C. The results of the chemical stability tests are illustrated in FIG. 4. As is shown in FIG. 4, small differences in chemical stability were observed. Formulation 12, with edetate buffer, produced the least number of hGH variants in the chemical stability test. However, the chemical stability test results indicated that all the formulations were comparable, suggesting that a variety of buffers could suitably be used to produce stable hGH liquid formulations of the type described in Table IV, above.

Example 5

Physical Stability of hGH Formulations with Various Tonicity Agents

Four hGH liquid formulations (Formulations 15 through 18) were prepared, as described in Table V, below, with 5 mg/ml somatotropin, citrate buffer, and with one of each of four different tonicity agents (mannitol, sorbitol, sucrose and trehalose). Note that none of the four formulations tested in this example contained additional stabilizers, such as a polymer stabilizer or non-ionic surfactant.

TABLE V

| | Formulation | | | |
|---|---|---|---|---|
| Composition | 15 | 16 | 17 | 18 |
| hGH concentration | 5 mg/ml | 5 mg/ml | 5 mg/ml | 5 mg/ml |
| Buffer | 5 mM Sodium Citrate | 5 mM Sodium Citrate | 5 mM Sodium Citrate | 5 mM Sodium Citrate |
| Tonicity Agent | 250 mM Mannitol | 250 mM Sorbitol | 250 mM Sucrose | 250 mM Trehalose |

Figure 5:
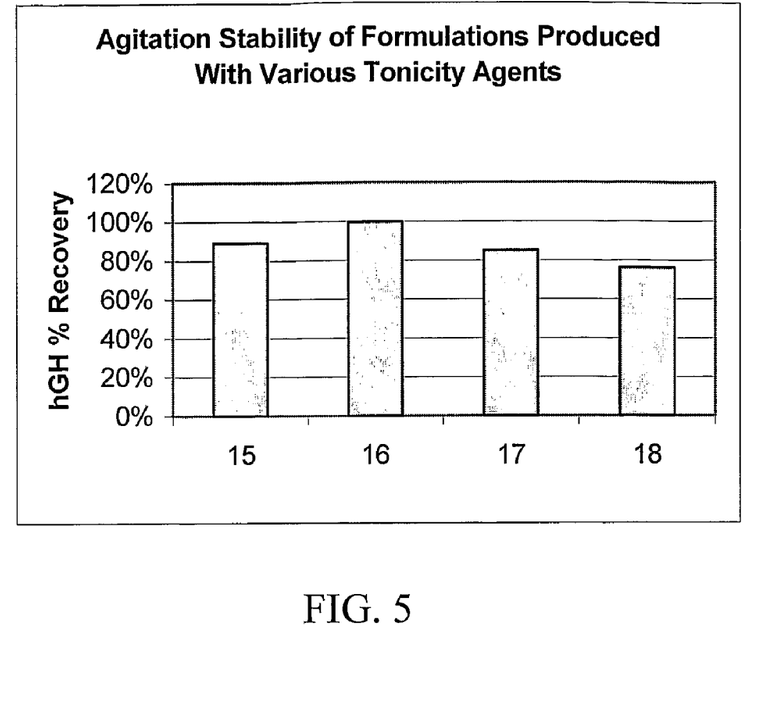
FIG. 5 is a bar graph of the total percent recovery of hGH, measured using protein absorbance analysis, from hGH liquid formulations prepared with various tonicity agents, after exposure to forced physical agitation, as described in Example 5.

Visual particulates were observed in samples of all four formulations, after forced agitation on a mechanical shaker at 250 RPM for 24 hours at room temperature (at about 25° C.). FIG. 5 is a plot of the percent hGH recovery observed in each formulation, by protein analysis, after the forced agitation step. The percent recovery of hGH from the formulation containing mannitol (Formula 15) was about 90%, a very good recovery rate for a formulation without any additional stabilizer. However, the best hGH recovery after agitation (almost 100%) was obtained with Formulation 16, a formulation prepared with sorbitol. This last result suggests that sorbitol has a stabilizing effect on hGH by itself and is a preferable tonicity agent to use in hGH liquid formulations.

Similar chemical stability was observed between the set of four hGH liquid formulations prepared with these four tonicity agents, as described above.

Example 6

Physical Stability of hGH Formulations with less than 0.1% Concentration of Surfactant Five different hGH liquid formulations (Formulations 19 through 23) were prepared, as described in Table VI, below. Each formulation contained 5 mg/ml somatotropin, citrate buffer, a tonicity agent (mannitol), and various concentrations of Polysorbate 20 (0, 0.02, 0.04, 0.06 and 0.08%).

TABLE VI

| Composition | Formulation | | | | |
|---|---|---|---|---|---|
| | 19 | 20 | 21 | 22 | 23 |
| hGH concentration | 5 mg/ml | 5 mg/ml | 5 mg/ml | 5 mg/ml | 5 mg/ml |
| Buffer | 5 mM Sodium Citrate | 5 mM Sodium Citrate | 5 mM Sodium Citrate | 5 mM Sodium Citrate | 5 mM Sodium Citrate |
| Tonicity Agent | 250 mM Mannitol | 250 mM Mannitol | 250 mM Mannitol | 250 mM Mannitol | 250 mM Mannitol |
| Surfactant | — | 0.02% Polysorbate 20 | 0.04% Polysorbate 20 | 0.06% Polysorbate 20 | 0.08% Polysorbate 20 |

Figure 6:
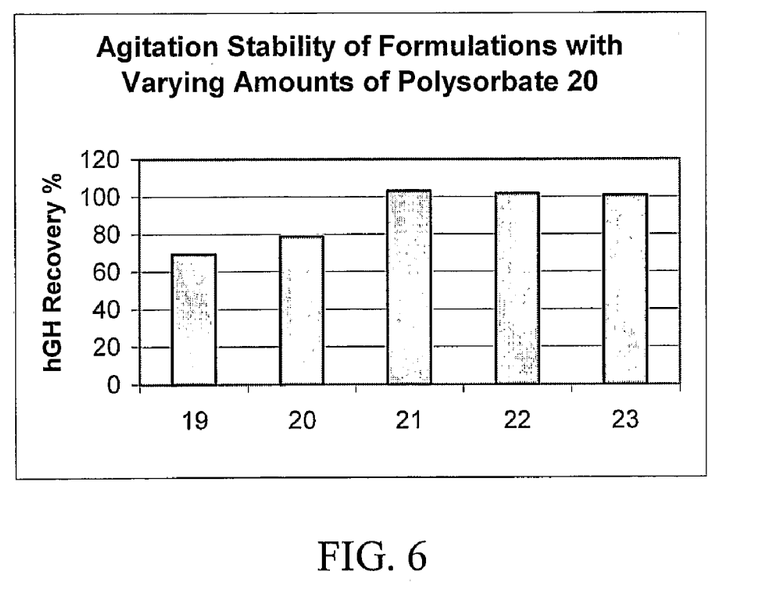
FIG. 6 is a bar graph of the total percent recovery of hGH, measured using protein absorbance analysis, from formulations prepared with various concentrations of a non-ionic polysorbate surfactant, after exposure to forced physical agitation, as described in Example 6.

As in Example 5, recovery of hGH was monitored by protein absorbance analysis after forced agitation at room temperature. The results of this assay are shown in FIG. 6. As shown in FIG. 6, 100% protein recovery was obtained from a formulations that contained a polysorbate concentration as low as 0.04% (Formulation 21), and improved recovery was observed even in formulations where the polysorbate concentration was as low as 0.02% (Formulation 20).

Example 7

Chemical Stability of hGH Liquid Formulations Containing Methionine as an Amino Acid Stabilizer Four formulations of liquid hGH, Formulations 24 through 27, were prepared as described in Table VII, below. Each formulation contained 5 mg/ml Genotropin® hGH protein, citrate buffer for a pH of 6, polysorbate surfactant, sorbitol, and PEG; with two of the formulations further containing methionine and two without methionine.

TABLE VII

| Composition | Formulation | | | |
|---|---|---|---|---|
| | 24 | 25 | 26 | 27 |
| hGH concentration | 5 mg/ml | 5 mg/ml | 5 mg/ml | 5 mg/ml |
| Buffer | 5 mM Sodium Citrate | 5 mM Sodium Citrate | 5 mM Sodium Citrate | 5 mM Sodium Citrate |
| Tonicity Agent | 250 mM Sorbitol | 250 mM Sorbitol | 250 mM Sorbitol | 250 mM Sorbitol |
| Surfactant Stabilizer | 0.06% Polysorbate 20 | 0.06% Polysorbate 20 | 0.06% Polysorbate 20 | 0.06% Polysorbate 20 |
| Polymer stabilizer | 1% PEG 3350 | 1% PEG 20000 | 1% PEG 3350 | 1% PEG 20000 |
| Amino Acid Stabilizer | — | — | 10 mM Methionine | 10 mM Methionine |

Chemical stability of each of the four formulations described immediately above was evaluated by reverse-phase HPLC (RP-HPLC). Similar to AEX-HPLC, RP-HPLC allows detection of hGH protein variants. Although these variants are known to be therapeutically active, the method provides a relative measure of hGH chemical stability.

Figure 7:
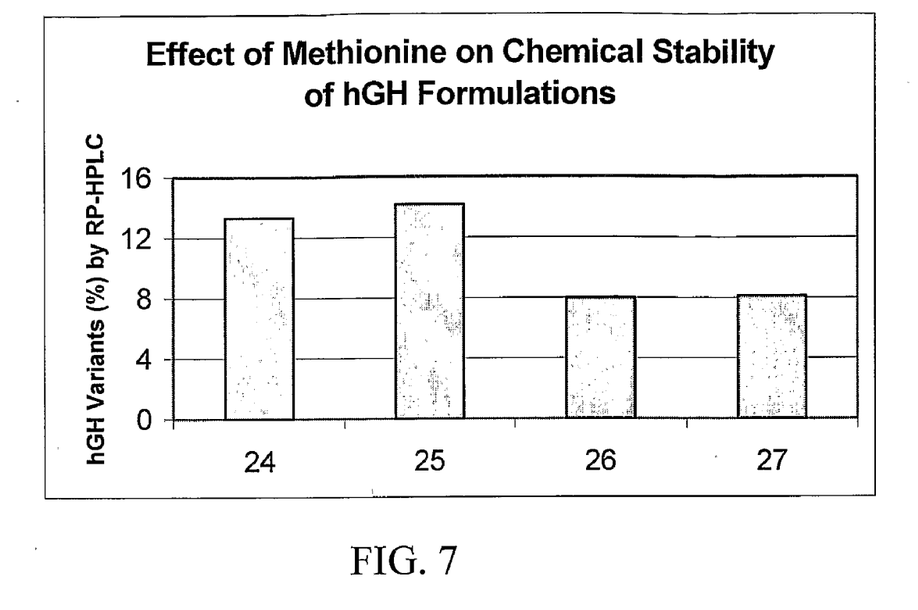
FIG. 7 is a bar graph of the total percent of hGH variants formed, measured using reverse phase HPLC, from hGH liquid formulations of the present invention, prepared with and without methionine, as described in Example 6, after 31 weeks of storage at 5° C.
Figure 8:
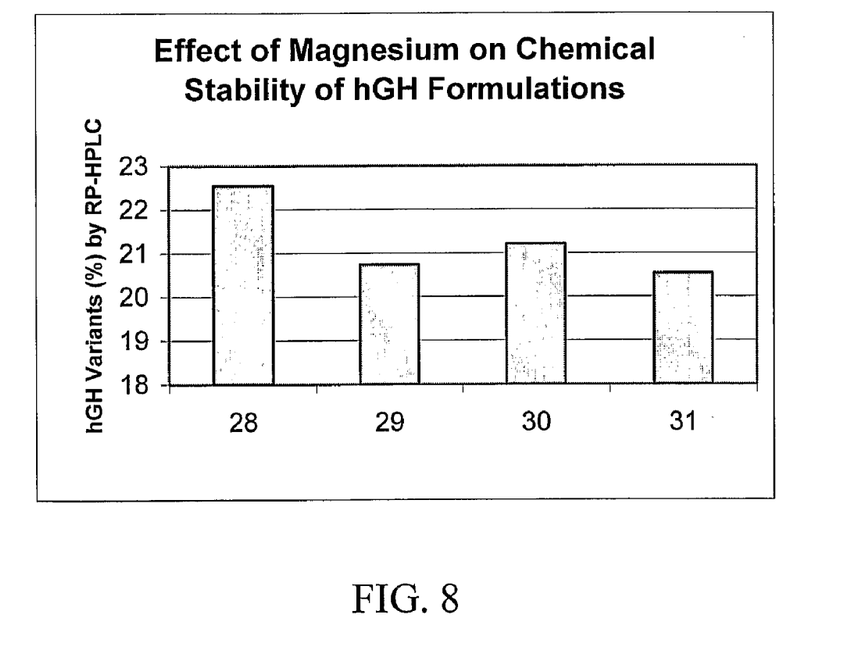
FIG. 8 is a bar graph of the total percent of hGH variants, measured using reverse phase HPLC, from hGH liquid formulations of the present invention, prepared with and without magnesium reagents, after about 2 months of storage at 5° C., as described in Example 8.

FIG. 7 is a plot of the results of the chemical stability analysis. As shown in FIG. 7, after 31 weeks at 5° C., RP-HPLC analysis indicated that the hGH formulations 26 and 27 that contained methionine had lower levels of protein variants as compared to formulations 24 and 25 that did not have methionine. The presence of added methionine did not have any stabilizing effect on hGH liquid formulations prepared earlier without PEG. Unexpectedly, however, it was found that methionine improved the chemical stability of the hGH liquid formulations tested in this Example, in which PEG polymer was not present. It is expected that formulations of the present invention could be also combined with other amino acid stabilizers (e.g. histidine, leucine, valine, and asparagine) to further stabilize hGH liquid formulations.

Example 8

Chemical Stability of hGH Formulations Containing Magnesium as a Divalent Cation Stabilizer Four hGH liquid formulations were prepared (Formulations 28 through 31), as described in Table VIII, below. Each formulation contained 5 mg/ml somatotropin, buffer, polysorbate surfactant, polymer stabilizer, and amino acid stabilizer. Two of the formulations (Formulations 29 and 31) also contained a Magnesium reagent, while the other two (Formulations 28 and 30) were prepared without Magnesium.

TABLE VIII

| Composition | Formulation | | | |
|---|---|---|---|---|
| | 28 | 29 | 30 | 31 |
| hGH concentration | 5 mg/ml | 5 mg/ml | 5 mg/ml | 5 mg/ml |
| Buffer | 5 mM Sodium Citrate | 5 mM Sodium Citrate | 10 mM Sodium Citrate | 10 mM Sodium Citrate |
| Surfactant Stabilizer | 0.06% Polysorbate 20 | 0.06% Polysorbate 20 | 0.06% Polysorbate 20 | 0.06% Polysorbate 20 |
| Polymer stabilizer | 1% PEG 20000 | 1% PEG 20000 | 1% PEG 3350 | 1% PEG 3350 |
| Additional Excipients | 250 mM Sorbitol, 10 mM Methionine | 250 mM Sorbitol, 10 mM Methionine | 250 mM Sorbitol, 10 mM Methionine | 250 mM Sorbitol, 10 mM Methionine |
| Magnesium Reagent | — | 2.5 mM Magnesium hydroxide | — | 3 mM Magnesium chloride |

Formulations 28 and 29 were analyzed by RP-HPLC, after 9 weeks storage at 25° C. Formulations 30 and 31 were analyzed after 8 weeks storage at 25° C. In both sets of formulations tested, lower levels of protein variants were observed in formulations where magnesium reagent was present (29 and 31), indicating improved hGH stability in the presence of magnesium.

These results are surprising because prior disclosures have described the stabilizing effect of calcium and zinc on hGH formulations (see U.S. Pat. No. 6,022,858), but not of magnesium. It is expected that formulations of the present invention could also be suitably combined with other divalent cations, such as calcium and zinc ions.

Example 9

Figure 9:
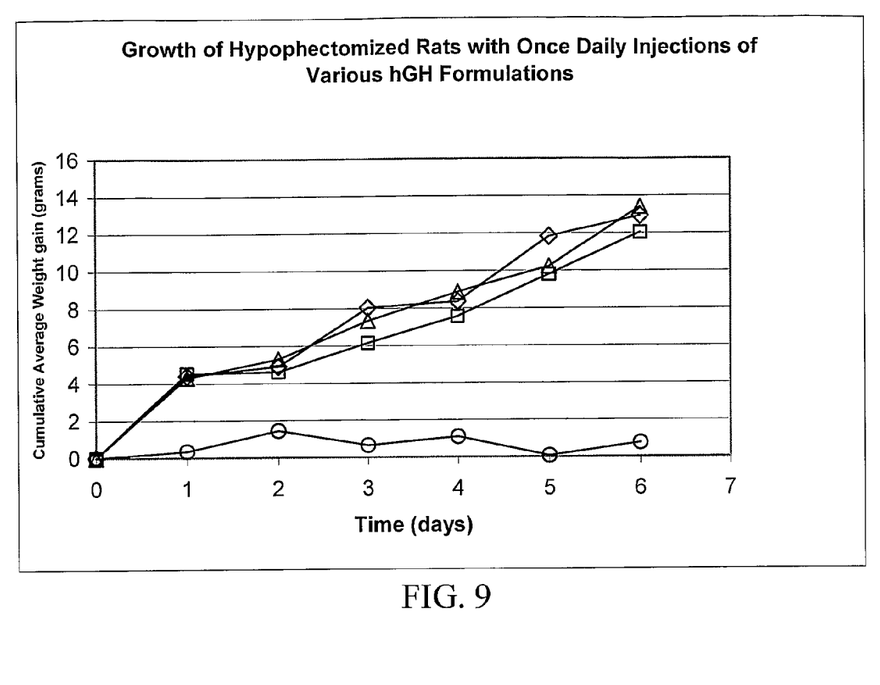
FIG. 9 is a plot of cumulative weight gain observed over time in hypophectomized rats, after being administered daily injections of hGH liquid formulations indicated therein, compared with rats injected with a placebo control solution containing no hGH ("PBS"). —□—represents Formulation 6 of Example 3. —Δ—represents Formulation 5 of Example 3. —◊—represents Formulation 8 of Example 3. —○—represents PBS control.

Bioactivity of hGH Formulations Prepared with Buffer, Non-ionic Surfactant, Polymer Stabilizer and Additional Excipients Formulations 5, 6, and 8 from Example 3, above, were tested for bioactivity after 6 weeks storage at 25° C. by injecting once daily into separate hyposectomized rats using a bioassay method for hGH that complies with the European Pharmacopoeia. Phosphate buffered saline (PBS) was injected as a control. The results of this study are illustrated in FIG. 9 and confirm that the formulations retained full bioactivity, which is to be expected if the formulations have adequate stability upon storage. All the hGH formulations resulted in expected level of rat growth whereas the control formulation (PBS) did not cause growth.

Example 10

Antimicrobial Effectiveness of hGH Formulations Containing Phenol as a Preservative Formulation 4 from Example 2 (see Table II), containing 5 mg/ml hGH, 10 mM sodium edetate buffer, 0.06% polysorbate 20, 1% PEG 3350, 0.3% phenol, and additional excipients, was tested for antimicrobial effectiveness against two representative microorganisms (*E. coli* and *A. niger*). The formulation had adequate antimicrobial activity as per acceptance criteria described in United States Pharmacopoeia, demonstrating that a preservative can be optionally added to the formulation with expected antimicrobial activity.

Example 11

Long-Term Storage of Liquid Genotropin Formulations

Six liquid formulations of hGH (Formulations 32 through 37) were prepared as per the Table IX, below, formulations contain 5 mg/mL somatotropin, citrate or edetate buffer (pH 6.0), 250 mM Sorbitol, (0.06% w/w) polysorbate 20, (1% w/w) PEG 3350 polymer, 10 mM methionine, and some of the formulations included magnesium chloride and some contained phenol as a preservative. Simulated versions of the commercially available NUTROPIN AQ® and NORDITROPIN® were also prepared, according to the formula provided on the product label (Y & Z). The composition of NUTROPIN AQ®, according to the product label, was: 5 mg/ml hGH, 10 mM sodium citrate, 8.7 mg/ml sodium chloride, 2 mg/ml (0.2%) Polysorbate 20, and 2.5 mg/ml (0.25%) phenol. The composition of this formulation has also been disclosed in U.S. Pat. No. 5,763,394. The composition of NORDITROPIN®, according to the product label, was: 3.3 mg/ml hGH, 0.67 mg/ml histidine, 40 mg/ml mannitol, 3 mg/ml (0.3%) Poloxamer 188, and 3 mg/ml (0.3%) phenol.

TABLE IX

| Formulation # | Sodium Citrate (mM) | Disodium Edetate (mM) | MgCl$_2$ (mM) | Phenol (% w/w) |
|---|---|---|---|---|
| 32 | 10 | — | — | — |
| 33 | — | 10 | — | — |
| 34 | 10 | — | 3 | — |
| 35 | — | 10 | 3 | — |
| 36 | 10 | — | 3 | 0.3 |
| 37 | — | 10 | 3 | 0.3 |

Figure 10:
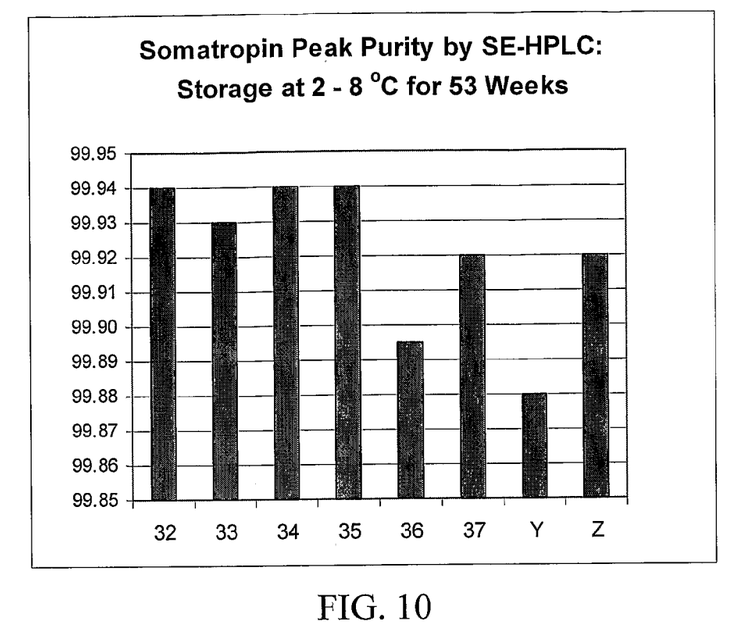
FIG. 10 is a bar graph of the total percent of hGH monomer, measured using size exclusion HPLC, from hGH liquid formulations of the present invention after about 53 weeks of storage at 5° C., as described in Example 11. Formulations 32-37 are formulations of the present invention and Y & Z are respectively the simulated NUTROPIN AQ® and NORDITROPIN SIMPLEXX® formulations.

Each of the formulation prepared as described in the present Example, above, was kept at proposed storage condition (2-8° C.) for 53 weeks. Samples were analyzed at 8, 16, 28 and 53 weeks. At each time point, samples were analyzed visually for presence of particulates, change in color, and clarity. pH measurements were also conducted. Presence of aggregates was monitored by SE-HPLC. All formulations, tested in this Example, remained visually clear, colorless and free of particles and did not show any significant change in pH. In addition, better than 99% hGH recovery, as measured by SE-HPLC, was obtained for all Formulations 32 through 37 of Table IX, and all the comparators tested in this Example, after being subjected to storage at 2 to 8° C. for 53 weeks (FIG. 10).

Each of the formulations was analyzed by Reverse Phase HPLC (RP-HPLC) to evaluate the formation of hGH protein variants after 53 weeks of refrigerated storage (5° C.). Although, at least some of the hGH variants detected by RP-HPLC are known to be therapeutically active, this method provides a measure of hGH recovery and can be used as an indication of hGH % purity.

Figure 11:
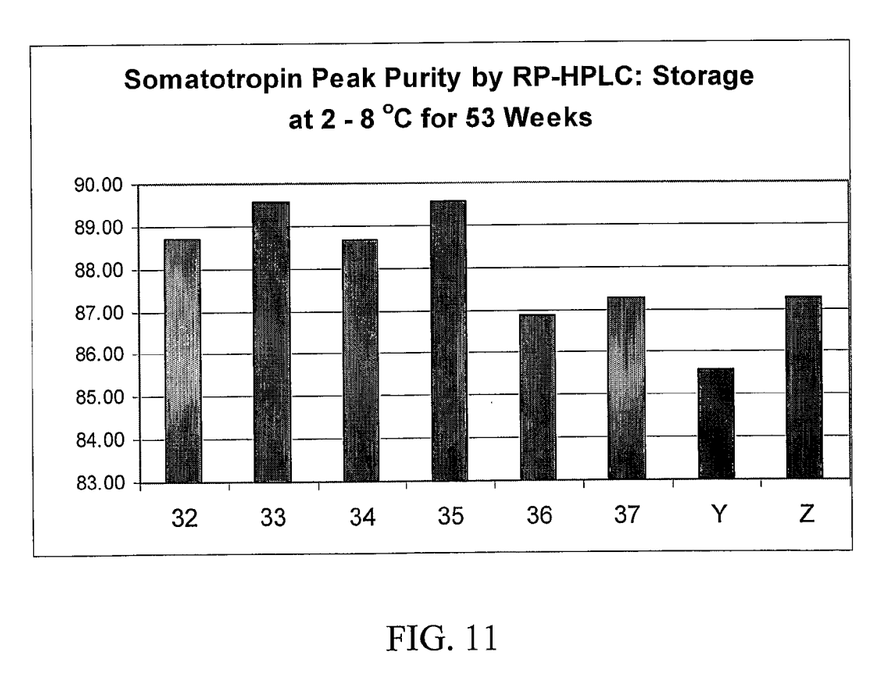
FIG. 11 is a bar graph of the total percent of hGH, measured using reverse phase HPLC, from hGH liquid formulations of the present invention after about 53 weeks of storage at 5° C., as described in Example 11. Formulations 32-37 are formulations of the present invention and Y & Z are respectively the simulated NUTROPIN AQ® and NORDITROPIN SIMPLEXX® formulations.

The results of the RP-HPLC assay are illustrated in FIG. 11. The results depicted therein clearly demonstrate that all the Genotropin formulations reported higher hGH % recovery after storage at 2 to 8° C. for 53 weeks. Formulations 33 & 35 (edetate buffer) reported the highest recovery % followed by Formulations 32 & 34 (citrate buffer). Genotropin formulations containing preservative (0.3% phenol) showed recovery in the range of 86.9-87.3%. In contrast, the simulated comparator products (NUTROPIN AQ® and NORDITROPIN®) showed recovery in the range of 85.5-87.3%.

Each of the formulations was also analyzed by Anion Exchange HPLC (AEX-HPLC) to evaluate the formation of hGH protein variants after 53 weeks of refrigerated storage (5° C.). This method provides a good measure of hGH chemical stability; specifically this assay method allows one to measure the levels of hGH variants formed over time, including deamidated species.

Figure 12:
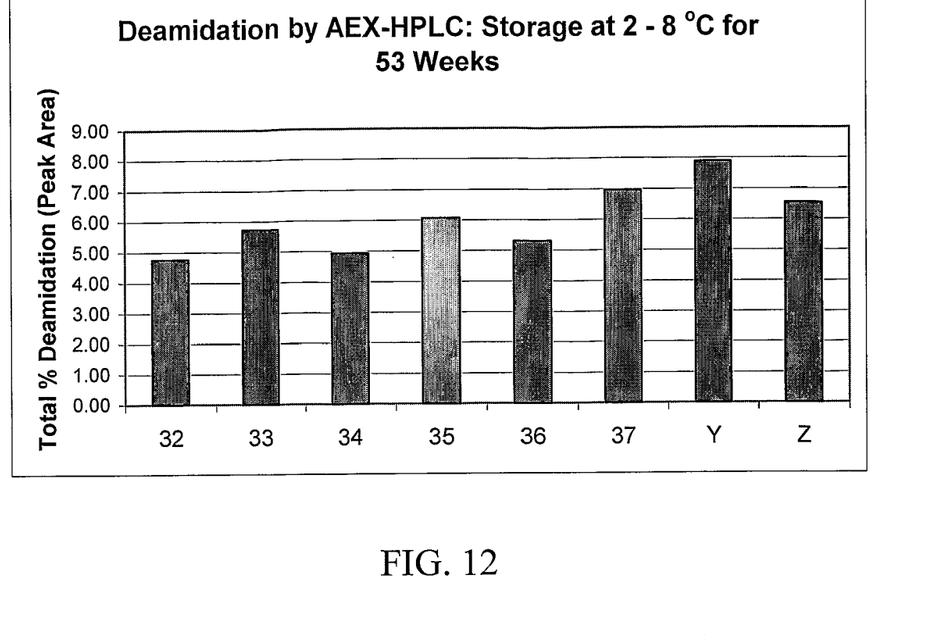
FIG. 12 is a bar graph of the total percent of deamidated hGH, measured using anion exchange HPLC, from hGH liquid formulations of the present invention after about 53 weeks of storage at 5° C., as described in Example 11. Formulations 32-37 are formulations of the present invention and Y & Z are respectively the simulated NUTROPIN AQ® and NORDITROPIN SIMPLEXX® formulations.
Figure 13:
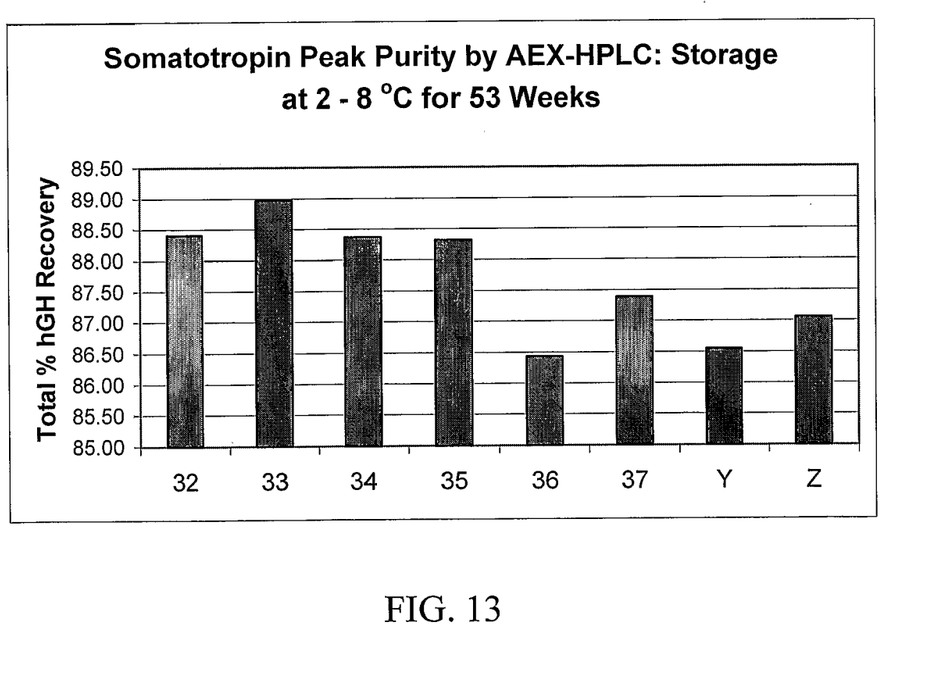
FIG. 13 is a bar graph of the total percent of hGH, measured using anion exchange HPLC, from hGH liquid formulations of the present invention after about 53 weeks of storage at 5° C., as described in Example 11. Formulations 32-37 are formulations of the present invention and Y & Z are respectively the simulated NUTROPIN AQ® and NORDITROPIN SIMPLEXX® formulations.

The results of the AEX-HPLC assay are illustrated in FIG. 12 (total deamidation) and FIG. 13 (hGH recovery). The results depicted therein demonstrate that AEX-HPLC detected lesser or similar levels of hGH variants for all Genotropin formulations than the comparators. The levels of variants are lower in Formulations 32 through 35 and 37, compared to those found in the simulated NUTROPIN AQ®® and NORDITROPIN®® (Formulations Y & Z in FIGS. 12 & 13). These results indicate that the Genotropin formulations show excellent chemical stability and physical stability relative to the two known, commercially available, hGH liquid formulations.

What is claimed is:

1. A formulation consisting of a therapeutically effective amount of a human growth hormone in an aqueous solution, a buffer that maintains the pH of the formulation at a pH of 5 to 7, a non-ionic polysorbate surfactant, a polymer stabilizer wherein said polymer stabilizer is a polyethylene glycol which has a molecular weight in the range of about 3000 to about 20,000, methionine, and one or more optional excipients selected from the group consisting of a divalent cation present in a magnesium salt selected from the group consisting of magnesium hydroxide, magnesium chloride, magnesium sulfate, magnesium citrate, and magnesium edentate; a tonicity agent; and a preservative, wherein the formulation remains stable after at least one freezing and subsequent thawing event.

2. The formulation of claim 1, wherein the human growth hormone is a recombinant form of human growth hormone.

3. The formulation of claim 2, wherein the recombinant form of human growth hormone is present in the formulation at a concentration of 0.1 mg/ml to 20 mg/ml.

4. The formulation of claim 1, wherein the buffer is selected from the group consisting of sodium citrate, sodium edentate, sodium succinate, and histidine hydrochloride.

5. The formulation of claim 1, wherein the non-ionic polysorbate surfactant is present at a concentration of about 0.02% to about 10%.

6. The formulation of claim 1, wherein the non-ionic polysorbate surfactant is selected from the group consisting of polysorbate 20 and polysorbate 80.

7. The formulation of claim 1, wherein the polyethylene glycol is present at a concentration of about 0.25% or about 1%.

8. The formulation of claim 1, wherein the tonicity agent is sorbitol.

9. The formulation of claim 1, wherein the preservative is selected from the group consisting of phenol and benzyl alcohol.

10. A formulation consisting of about 0.1 mg/ml to about 20 mg/ml of a recombinant form of human growth hormone in an aqueous solution, a citrate or edentate buffer that maintains the formulation at a pH of about 5 to about 7, about 0.04% to about 5% (w/w) of a polysorbate surfactant, about 0.25% or about 1% (w/v) of polyethylene glycol, methionine, and one or more optional excipients selected from the group consisting of a sufficient concentration of sorbitol for the formulation to be approximately isotonic, magnesium chloride or magnesium hydroxide, and a preservative, wherein the formulation remains stable after at least one freeze thaw event.

11. The formulation of claim 10, wherein the preservative is phenol or benzyl alcohol.

12. The formulation of claim 10, wherein at least about 90% of the recombinant form of human growth hormone remains in solution after exposure of the formulation to three or more freeze-thaw events.

13. The formulation of claim 10 where the formulation is stable at about 2° C. to about 8° C. for at least 52 weeks.

14. The formulation of claim 13 wherein after 52 weeks at about 2° C. to about 8° C. at least one of
 (i) total aggregate as measured by size exclusion HPLC is less than about 0.5%,
 (ii) total deamidation as measured by anion exchange HPLC is less than about 7%, or
 (iii) the recombinant form of human growth hormone recovery as measured by reverse phase HPLC is greater than or equal to 85%.

* * * * *

UNITED STATES PATENT AND TRADEMARK OFFICE
CERTIFICATE OF CORRECTION

| | | |
|---|---|---|
| PATENT NO. | : 8,338,374 B2 | Page 1 of 1 |
| APPLICATION NO. | : 10/583923 | |
| DATED | : December 25, 2012 | |
| INVENTOR(S) | : Manpreet S. Wadhwa et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 45 days.

Signed and Sealed this
Fifteenth Day of July, 2014

Michelle K. Lee
*Deputy Director of the United States Patent and Trademark Office*